US007582858B2

(12) United States Patent
Faris et al.

(10) Patent No.: US 7,582,858 B2
(45) Date of Patent: Sep. 1, 2009

(54) APPARATUS AND METHOD OF MOVING MICRO-DROPLETS USING LASER-INDUCED THERMAL GRADIENTS

(75) Inventors: Gregory W. Faris, Menlo Park, CA (US); Kenneth T. Kotz, Medford, MA (US); Kyle Noble, San Antonio, TX (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 10/597,372

(22) PCT Filed: Jan. 21, 2005

(86) PCT No.: PCT/US2005/002033

§ 371 (c)(1), (2), (4) Date: Sep. 28, 2006

(87) PCT Pub. No.: WO2005/069964

PCT Pub. Date: Aug. 4, 2005

(65) Prior Publication Data

US 2008/0105829 A1 May 8, 2008

Related U.S. Application Data

(60) Provisional application No. 60/538,951, filed on Jan. 23, 2004.

(51) Int. Cl.
*H01S 1/00* (2006.01)
*H01S 3/00* (2006.01)
*H05H 3/02* (2006.01)
*C12Q 1/68* (2006.01)

(52) U.S. Cl. .......................................... 250/251; 435/6

(58) Field of Classification Search ............ 250/423 R, 250/429, 251; 137/808–828; 417/207, 208
See application file for complete search history.

(56) References Cited

U.S. PATENT DOCUMENTS 3,808,550 A * 4/1974 Ashkin ....................... 250/251

(Continued)

OTHER PUBLICATIONS

Addison, Anica; Critical Angle of Non-Horizontal Surface for a Drop at Static Equilibrium; May 5, 2000.

(Continued)

*Primary Examiner*—Jack I Berman
*Assistant Examiner*—Brooke Purinton
(74) *Attorney, Agent, or Firm*—Guerin & Rodriguez, LLP; Michael A. Rodriguez

(57) ABSTRACT

Described are an apparatus and method of moving micro-droplets. A surface has a liquid phase thereon. In the liquid phase is a droplet. Focused at an edge of the droplet is a beam of light. The light beam produces a thermal gradient sufficient to induce the droplet to move according to the Marangoni effect. The movement-inducing thermal gradient may appear within the droplet or within the liquid phase. The composition of the droplet, the liquid phase, and wavelength of the light beam can cooperate to cause heating within the droplet, liquid phase, or both. For example, an infrared laser can cause vibration of an O-H stretch in an aqueous droplet (or in the liquid phase). As another example, adding dye to a droplet or to the liquid phase enables absorption of light from an Argon ion laser. The apparatus and method find particular use in biological and chemical high-throughput assays.

34 Claims, 5 Drawing Sheets

U.S. PATENT DOCUMENTS

| | | | | |
|---|---|---|---|---|
| 5,275,787 | A | 1/1994 | Yuguchi et al. | |
| 5,856,200 | A | 1/1999 | Krause et al. | |
| 6,469,779 | B2 * | 10/2002 | Baer et al. | 356/36 |
| 6,539,956 | B1 * | 4/2003 | Wolke et al. | 134/61 |
| 6,620,620 | B1 | 9/2003 | Anderson et al. | |
| 6,734,436 | B2 | 5/2004 | Faris et al. | |
| 2002/0001544 | A1 | 1/2002 | Hess et al. | |
| 2003/0021694 | A1 * | 1/2003 | Yevin | 417/207 |
| 2003/0086824 | A1 | 5/2003 | Sasaki et al. | |
| 2003/0224528 | A1 | 12/2003 | Chiou et al. | |
| 2004/0115830 | A1 * | 6/2004 | Touzov | 250/251 |
| 2004/0191127 | A1 | 9/2004 | Kornblit et al. | |
| 2004/0211659 | A1 * | 10/2004 | Velev | 204/164 |

OTHER PUBLICATIONS

Garnier, Nicolas, Roman O. Grigoriev, Michael F. Shatz; Optical Manipulation of Microscale Fluid Flow; Physical Review Letters; Jul. 30, 2003; 054501-1 to 054501-4; vol. 92, No. 5; The American Physical Society, USA.

Grigoriev, Roman O., Michael F. Schatz; Optically Controlled Mixing in Microdroplets; American Institute of Aeronautics and Astronautics; 1-11.

Grigoriev, Roman O.; Opto-Microfluidics, http://cns.physics.gatech.edu/~roman/muflu.html.

Ichikawa, Masatoshi, Kenichi Yoshikawa; Optical transport of a single cell-sized liposome; Applied Physics Letters; Dec. 31, 2001; 4598-4600; vol. 79, No. 27; American Institute of Physics.

Kulin, Simone, Rani Kishore, Kristian Helmerson, Laurie Locascio; Optical Manipulation and Fusion of Liposomes as Microreactors; Langmuir; Jun. 26, 2003; 8206-8210; vol. 19, No. 20; American Chemical Society.

Pearson, Helen; Chemists shrink beakers into drops; Nature; Sep. 10, 2003; Nature News Service/Macmillan Magazines Ltd.

Velev, Orlin D., Brian G. Prevo, Ketan H. Bhatt; On-chip manipulation of free droplets; Nature; Dec. 4, 2003; 515-516; vol. 426; Nature Publishing Group.

* cited by examiner t = 0.00s
80
84
96 t = 1.00s
98
96 t = -2.00s
88
80
92
84
96 t = 0.67s
98
96

APPARATUS AND METHOD OF MOVING MICRO-DROPLETS USING LASER-INDUCED THERMAL GRADIENTS

RELATED APPLICATION

This application claims the benefit of the filing date of U.S. Provisional Application, Ser. No. 60/538,951, filed Jan. 23, 2004, titled "Optical Microfluidics," the entirety of which provisional application is incorporated by reference herein.

FIELD OF THE INVENTION

The invention relates generally to optical microfluidics. More particularly, the invention relates to an apparatus and method for moving micro-droplets using laser-induced thermal gradients.

BACKGROUND

In its perpetual struggle against sickness and disease, humankind needs rapid and inexpensive means of detecting biological molecules responsible for human infirmities. Modern man faces a gamut of threats to human health, including biological warfare, emerging drug-resistant forms of infectious diseases, rising incidences of food contamination by pathogenic bacteria, infectious diseases in underdeveloped countries, and manmade environmental hazards. There is a sense of urgency to find appropriate technological solutions for diagnosing and monitoring biological threats to human health. Progress in biomedical assays, diagnostics and biological science, however, often encounters an inability to process large numbers of samples with a satisfactory degree of throughput.

Microfluidics devices have become a potential source of hope in meeting the needs for high-throughput measurements. Microfluidics possesses the potential for high throughput, rapid reaction kinetics, and small sample consumption. Industry has produced many types of microfluidic devices, typically using electrophoretic or electroosmotic forces to move small fluid volumes. Current approaches to microfluidic control include lateral flow structures, electrophoretic methods, and pneumatic designs. Each of these approaches has certain limitations that have slowed the pace of microfluidics-device development, such as problems with scaling, assay reconfigurations, poor sample-use efficiency, and considerable complexity of circuitry.

Lateral flow structures, for example, that rely on microporous membranes have properties and performance that are difficult to control. Electrophoretic methods for controlling the flow of fluid are not compatible with many solvents, and can result in the separation of biological molecules during steps when solution homogeneity is desired. Further, voltage leakage between microfluidic channels can limit the precision with which the methods can control the flow of fluid. Pneumatic designs have been successfully implemented using soft-lithography techniques, but these implementations are limited to elastomer materials that are not compatible with many types of biological assays. Some lithographic methods produce fixed networks of microconduits (i.e., micropipes) that make reconfiguration difficult and, in effect, result in single-use devices. There is, therefore, a need for microfluidics apparatus and techniques that can avoid or mitigate the aforementioned disadvantages of such current approaches.

SUMMARY

In one aspect, the invention features a method of moving droplets. A liquid phase is provided on a surface. A droplet is dispensed into the liquid phase, which is immiscible with the droplet. A beam of light is focused at an edge of the droplet in the immiscible liquid phase to produce a thermal gradient sufficient to induce the droplet to move.

In another aspect, the invention features an apparatus for moving droplets. The apparatus includes a surface and a droplet disposed on the surface. A light source produces a focused beam of light. The apparatus also includes means of directing the light beam at the droplet disposed on the surface. The light beam heats the droplet to cause a thermal gradient to form across the droplet sufficient to induce the droplet to move across the surface.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Figure 1:
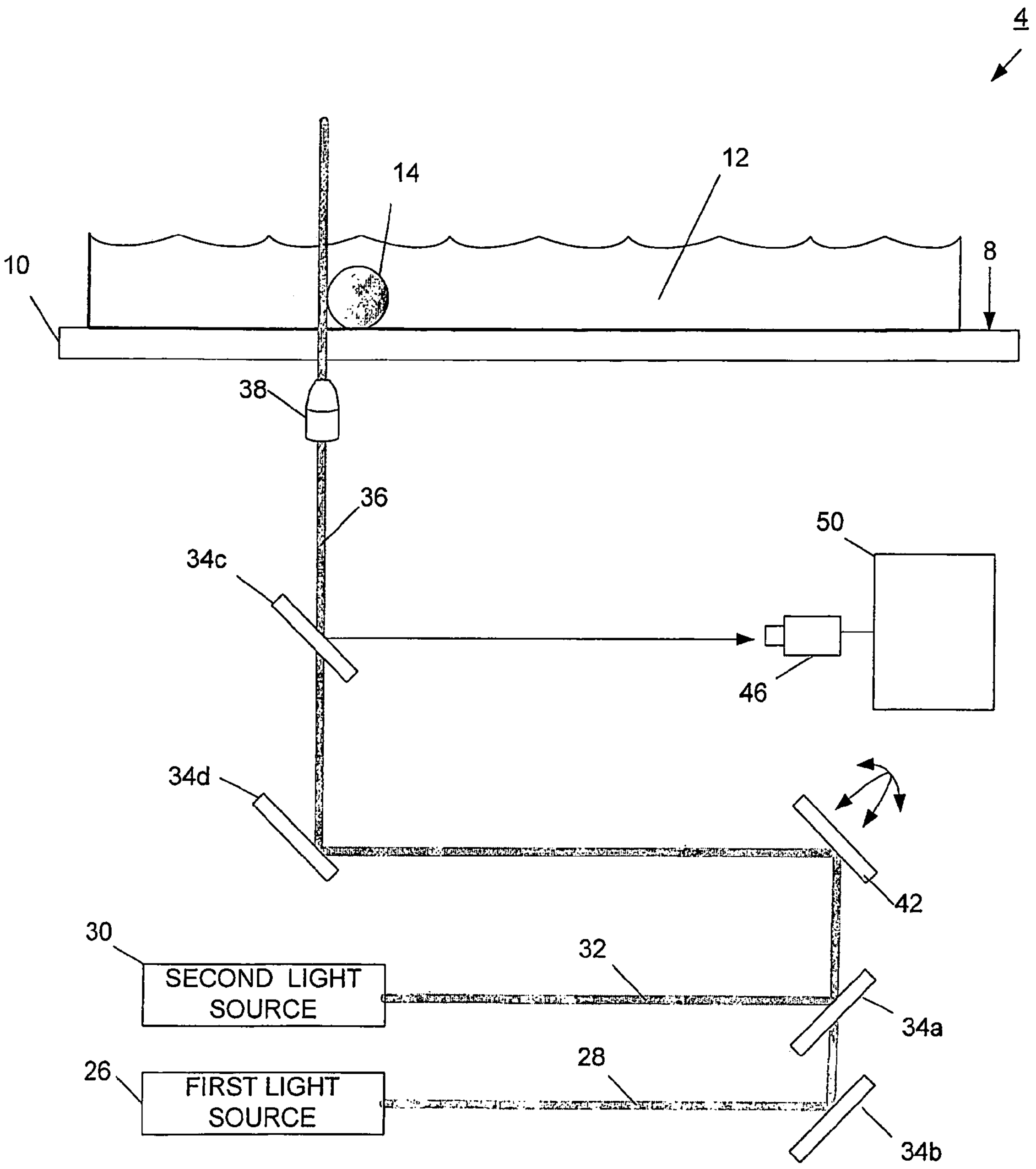
FIG. 1 is a diagram of an embodiment of an apparatus for optically moving droplets using a focused laser beam in accordance with the invention.

The present invention features methods, apparatus, and microfluidics devices for optically moving micro-droplets using laser-induced thermal gradients. As used herein with respect to droplets and microfluidics devices, the prefix "micro" means generally a very small amount, i.e., microscale, and does not refer to any particular precise measure (i.e., one-millionth of a unit). Deposited on a surface of a substrate are one or more micro-droplets. A substrate, as used herein, generally refers to any material having a surface onto which one or more micro-droplets may be deposited and across which such droplets may be moved. The term "substrate" can also refer to a particular substance (e.g., carried within a droplet) upon which an enzyme acts. On the surface, a liquid phase, immiscible with the liquid of the droplets, surrounds the droplets (e.g., to prevent evaporation of the droplets and to improve a contact angle between the droplets and the surface). The immiscible liquid phase may be comprised of multiple, different liquids of different densities that produce a fluid-to-fluid interface at which the droplets are suspended. Directed at or near an edge of a selected droplet, a laser beam produces a thermal gradient either across the droplet or within the surrounding liquid phase (or both). The composition of the droplet, liquid phase, and wavelength of the laser beam cooperate to determine where the thermal gradient forms.

The thermal gradient caused by the laser beam induces a surface energy or surface tension gradient on the surface of the droplet sufficient to move the droplet in accordance with the Marangoni effect. Surface tension forces produced by the invention are capable of moving droplets of sizes ranging from 1.7 μL to 14 pL in volume at speeds approximating 3 mm/s. Examples of applications for the present invention include identification of genes, protein-detection assays, single-cell analysis, combinatorial chemistry, and drug development and screening. Exemplary implementations of protection-detection assays are described in U.S. Pat. No. 6,815,210, issued Nov. 9, 2004 to Profitt et al; of identification of a gene, in U.S. Pat. No. 6,841,351 issued Jan. 11, 2005 to Gan et al.; of single-cell analysis, in U.S. Pat. No. 6,673,541, issued Jan. 6, 2004 to Klein et al.; of combinatorial chemistry, in U.S. Pat. No. 6,841,258, issued Jan. 11, 2005 to Halverson et al; and of drug development and screening, in U.S. Pat. No. 6,046,002, issued Apr. 4, 2000 to Davis et al: the entirety of these patents are incorporated by reference herein in their entirety.

Advantages of the present invention include: (1) droplets are dispensable on demand; (2) assays are dynamically reconfigurable; (3) random access to sites on a microfluidic device is possible; and (4) microfluidic devices (substrates) embodying the invention are generally disposable, not requiring expensive or time-consuming fabrication. The present invention also dispenses with features typically needed by other microfluidic techniques, such as valves and pumps, "on-chip" optical and electrical circuitry, and the use of laser pulses in order to fuse droplets.

FIG. 1 shows an embodiment of an apparatus 4 for controlling the movement of droplets in accordance with the principles of the invention. The apparatus 4 includes a surface 8 of a substrate 10, an immiscible, non-volatile liquid 12 disposed on the surface 8, and a droplet 14 surrounded by the liquid 12. If the liquid 12 is volatile, means is provided to mitigate evaporation of this liquid such as the use of a cover over the liquid. Preferably, the droplet 14 is immersed fully in the liquid 12, but full immersion is not required to practice the invention. In one embodiment, the droplet is formed from an aqueous fluid (e.g., water and a buffered saline). The droplet 14 can contain other compounds, such as biomolecules (e.g., nucleotidic or peptidic) and surfactants (e.g., anionic, cationic, nonionic, or amphoteric). In practice, the droplet 14 can range in size from approximately 30 μm to 1500 μm in diameter.

Preferably, the surface 8 upon which the droplet 14 is disposed is substantially planar, although the surface 8 may have any contour suitable for microfluidic movement. The substrate 10 can have one of a variety of forms, e.g., wafer, slides, plates, or a standard polystyrene Petri dish. An exemplary implementation of the substrate 10 is a microfluidics device (or "lab-on-a-chip"), such as the microfluidics device described in U.S. Pat. No. 6,734,436, issued to Faris et al. on May 11, 2004, and which is incorporated by reference herein.

By surrounding the droplet 14, the liquid 12 prevents evaporation of the droplet 14. Another advantage gained by using the liquid 12 is to increase the mobility of the droplet 14 by producing large contact angles between the droplet 14 and the surface 8, described below in FIG. 2. The influence of the surrounding liquid 12 on the droplet contact angle is described by A. Marmur, "Adhesion and wetting in an aqueous environment: Theoretical assessment of sensitivity to the solid surface energy," Langmuir 20, 1317-1320 (2004), which is incorporated by reference herein. Large contact angles reduce the force needed to move the droplet. In one embodiment, this liquid 12 includes 1-decanol (i.e., an organic liquid). Saturating the liquid 12 beforehand with water can sufficiently slow any aqueous dissolution of the droplet 14 into the surrounding fluid 12.

A light source 26 emits a light beam 28. In one embodiment, the light source 26 includes a near-infrared (NIR) laser (e.g., 30 mW) that generates an infrared laser beam with a 1550 nm wavelength. This wavelength can operate to heat an aqueous droplet or the surrounding liquid 12 through the vibrational excitation of the first overtone/combination band of the O—H stretch vibration in water. The water O—H vibrational absorption can absorb approximately 10% of this infrared light. An advantage to using infrared light is to avoid potential complications caused by unintended excitation of electronic transitions and chromophore photochemistry.

In another embodiment, the light source 26 includes an Argon ion laser (e.g., 10-200 mW) for producing a visible (i.e., green light) laser beam. In this embodiment, the droplet 14 or the surrounding liquid 12 (depending upon which is to form a thermal gradient) includes dye—e.g., FD&C Red No. 40, McCormick & Co., Inc.—to produce optical absorption of the laser beam and, as a result, to generate heat through the electronic excitation of the dye molecules.

The apparatus 4 also includes a second light source 30 for use, in general, in embodiments where the first light source 26 emits light that is invisible to the unaided human eye. The second light source 30 produces a visible light beam 32, which, when overlapped with the first light beam 28, enables a technician to track visually the position of the invisible light beam 28. In one embodiment, the second light source 30 includes a HeNe laser for generating a visible laser beam at a 633 nm wavelength.

Cold mirrors 34*a* and 34*b* operate to align the light beams 28, 32 to produce a composite light beam 36. Cold mirror 34*c* directs the light beam 36 to an aspheric lens 38 (with, e.g., a 7 mm aperature). The lens 38 focuses the composite light beam 36 onto the imaging plane of an inverted microscope stage (i.e., that is supporting the substrate 10). In this embodiment, the light beam 36 is incident upon the surface 8 from below (i.e., through the substrate 10), and the substrate 10 is transparent to the particular wavelength(s) of the light beam 36. In other embodiments, the composite light beam 36 can be directed to the droplet 14 or liquid 12 from above the surface 8 (i.e., not through the substrate 10), without departing from the principles of the invention.

A motorized steering mirror 42 situated in the path of the light beam 36 controls the position of the light beam 36 on the image plane of the inverted microscope stage. Faster motion of the laser beam 36 can be achieved using non-mechanical means of steering the laser such as acoustooptic, electrooptic, or liquid crystal devices. The position of the laser beam 36 relative to the droplet 14 may also be controlled by moving the microscope stage. A cold mirror 34*d* directs images of droplet movement induced by the light beam 36 to a camera 46 connected to a computer system 50. A technician can use this same optical system for controlling the light beam 36 and for observing reactions between fused droplets.

Figure 2:
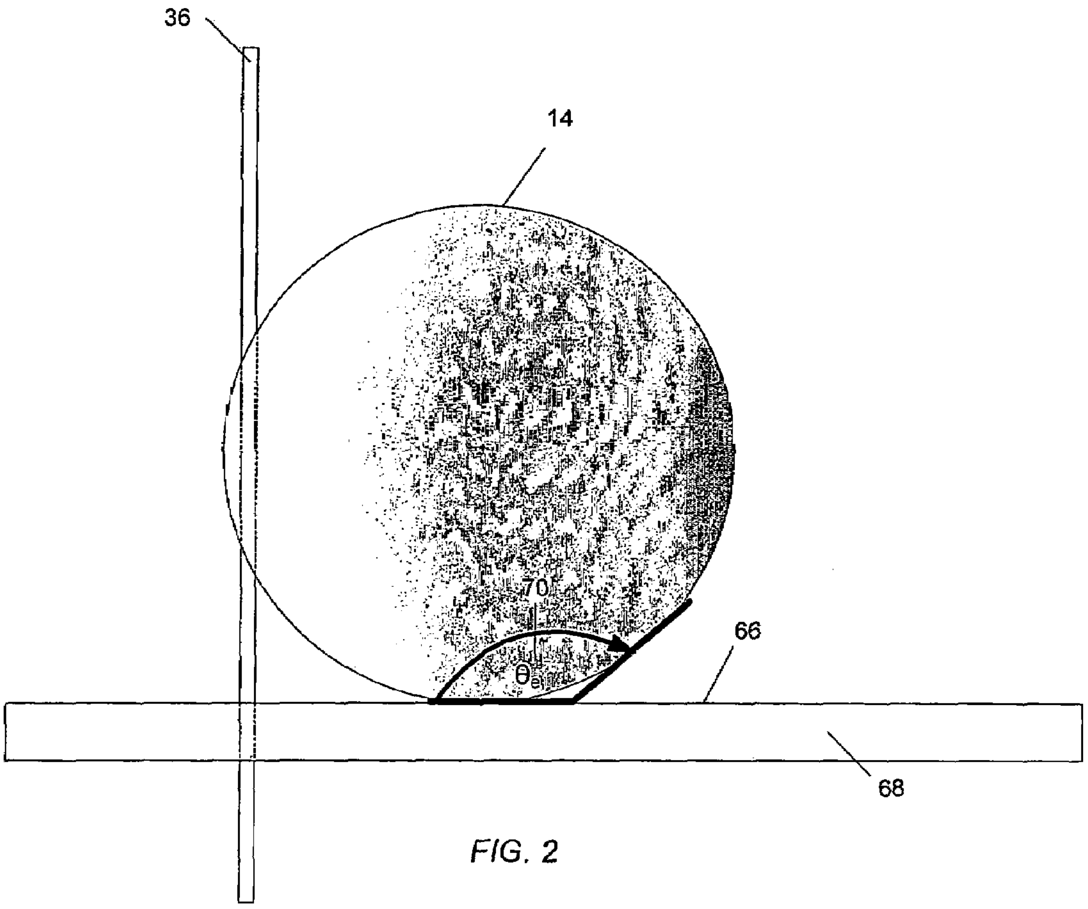
FIG. 2 is a diagram illustrating an example of a contact angle formed between a droplet and a surface.

FIG. 2 shows the droplet 14 (e.g., immersed in decanol) in contact with a solid surface 66 of a substrate 68. The droplet 14 may touch the surface 66 directly or indirectly (i.e., through the liquid 12). For droplets of microscale sizes, surface forces are dominating factors for the substantially spherical shape and movement of droplets over the surface 66. An angle 70 ($\square_E$) forms where the droplet 14 contacts the solid surface 66, referred to as a contact angle, is an indicator of the strength of adhesion of the droplet 14 to the surface 66. In the apparatus 4 of the invention, contact angles of the droplet 14 generally approach 180°, with a small percentage of the droplet perimeter contacting the surface (less than 10% of the droplet diameter). Such large contact angles correspond to low surface adhesion. When the droplet 14 is at equilibrium, contact angles on opposite edges of the droplet are symmetric. Force, when applied to the droplet 14, breaks the symmetry between the contact angles, causing a difference between the advancing and receding contact angles, referred to as contact angle hysteresis. The force needed to move the droplet 14 increases with contact angle and contact angle hysteresis. Conversely, a low contact angle hysteresis facilitates droplet movement.

The present invention uses surface tension to move droplets. Surface tension and surface energy generally decrease as temperature increases. Droplets move toward colder regions of the surface where the surface energy is higher, an effect called the thermal Marangoni effect. When the light beam 36 tangentially touches or passes through the droplet 14, a thermal gradient forms across the droplet 14. The droplet 14 heats, for example, by the vibration of O—H stretch of water or the excitation of dye molecules in a dye-carrying droplet. Calculations show that the temperature rise across the width of the droplet 14 is at most approximately 10° C., which should not affect chemical kinetics or the stability of thermally sensitive molecules in a droplet assay. The light-to-dark shading of the droplet 14 provides a graphical illustration of the thermal gradient, the lighter-colored regions of the droplet representing the warmer portions of the temperature gradient, the darker-colored regions representing the cooler portions. This temperature gradient induces a surface energy gradient sufficient to move the droplet 14 in accordance with the Marangoni effect.

FIGS. 3A through 3D provide a sequence of diagrams illustrating an exemplary application of the present invention for a chemical assay. The diagrams correspond to a sequence of video frames produced by a camera (such as camera 46 of FIG. 1). Each image is a view of the droplet motion and mixing from below the substrate 10. In this sequence, a first droplet 80 contains an enzyme, e.g., horseradish peroxidase, in phosphate buffer (0.1 M pH 6.2), and a second droplet 84 contains an excess of chromogenic substrates: 2,2'-azino-bis (3-ethylbenzthiazoline-6-Sulfonic acid) diammonium salt (ABTS), and hydrogen peroxide.

Figures 3A, 3B, 3C, 3D:
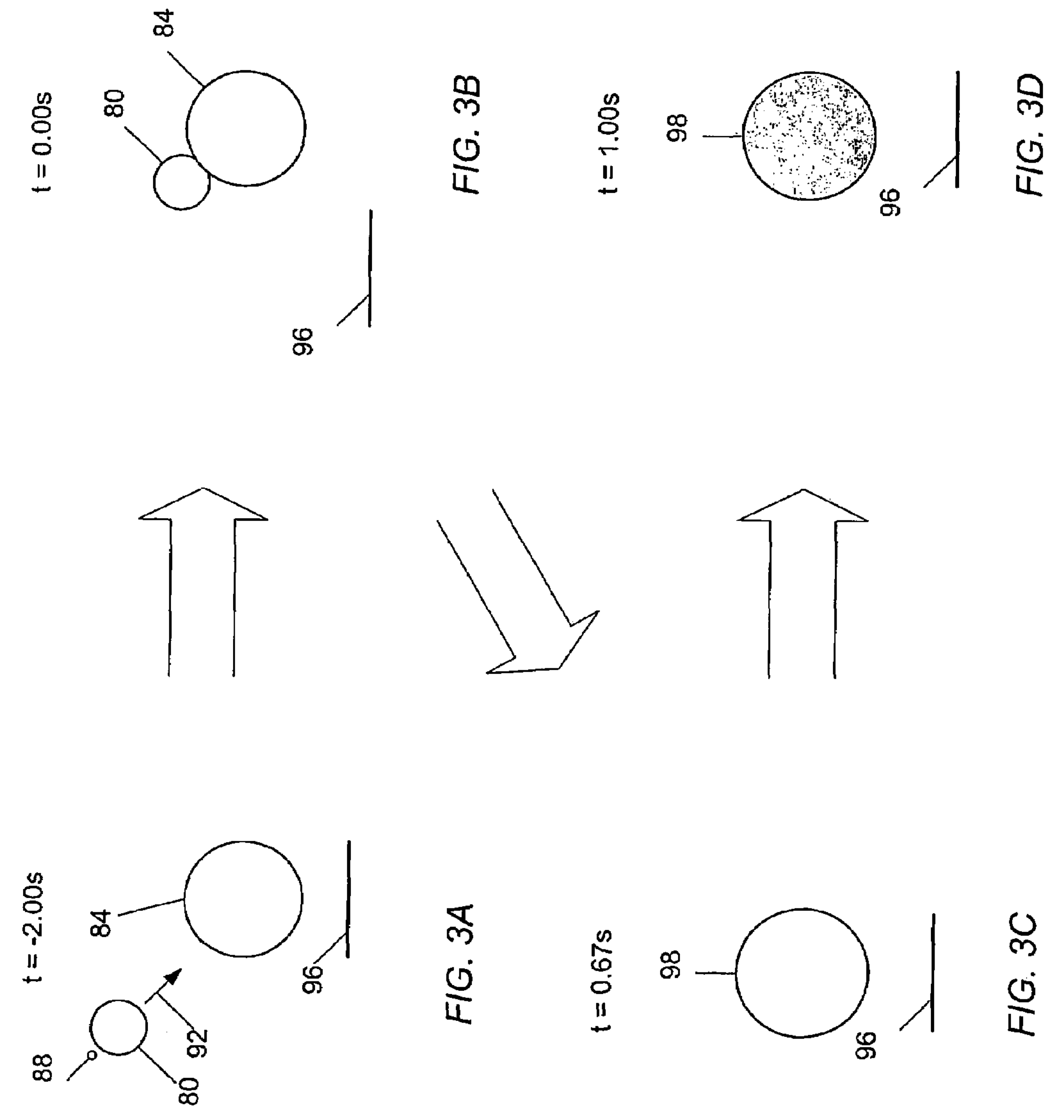
FIG. 3A, FIG. 3B, FIG. 3C, and FIG. 3D are an exemplary sequence of images corresponding to the movement and mixing of droplets in accordance with the principles of the invention.

FIG. 3A shows a spot of light produced by a laser beam (pointed to by arrow 88), focused adjacent to the first droplet 80 at time t=−2.00 seconds. The laser beam 88 induces the droplet 80 to move towards the second droplet 84 in accordance with to the Marangoni effect, as described above. Arrow 92 identifies the direction of droplet motion. Line 96 provides a scale for the size of the droplets 50, 84, representing 250μm. In FIG. 3B, the first droplet 80 encounters the second droplet 84, defined as time t=0.00s, and the droplets 80, 84 spontaneously fuse to produce droplet 98. Droplet volume is conserved the droplets 80, 84, as shown in FIG. 3C. In FIG. 3D, the HRP enzyme in the first droplet 80 reacts with the substrates in the second droplet 84, oxidizing the ABTS and resulting in the darker-colored droplet 98 (i.e., dark green). Reactions are observed in droplets having diameters as small as 40 μm and at concentrations of approximately 3.7 μM, which corresponds to approximately 125 attomoles of reacting enzyme. Detection of zeptomoles of reacting enzymes may be attainable by reducing droplet diameter. This same colorization—serving as an indicator of a reaction—also occurs if the laser beam 88 is used to move instead the second droplet 84 into contact with the first droplet 80. This reciprocal observation suggests that moving the first droplet 80 using the laser beam does not heat the contents of the droplet 80 beyond an irreversible denaturing point of the HP enzyme.

In FIG. 3C and FIG. 3D, complete mixing of the droplet contents occurs in a shorter period than the time between successive video frames (here, 33 ms). The fusion process may account for this rapid mixing: in contrast, diffusion can require 10 to 30 seconds to produce comparable content mixing, depending upon the diffusion coefficients of the solutes. Thus, the rapid mixing of liquids produced by the present invention provides an advantage over channel-based methodologies that have long diffusion-limited mixing durations.

An explanation for the rapid mixing of fused droplets may be attributable to surface energy. The fused droplet 98 has a lower surface area and, thus, a lower surface energy than the two droplets 80, 84 prior to fusion. The change in surface energy is converted largely to kinetic energy, causing droplet oscillation dampened by viscosity. One hundred micron diameter water droplets in decanol have an oscillation frequency of 1.5 KHz and a damping time of 110 μs (based on small oscillations and water/decanol interfacial surface tension theory). A characteristic velocity for the mixing process can be defined by equating the change in surface energy from droplet fusion to the kinetic energy of the droplet volume. This velocity scales as $D^{1/2}$, where D is the droplet diameter; the Reynolds number scales $D^{1/2}$. Observations of the dynamics of merging droplets show contact surface velocities similar to this characteristic velocity. For 100-μm diameter droplets, for example, the characteristic velocity is approximately 50 cm/s, corresponding to a Reynolds number of approximately 70. For flow over a cylinder, Reynolds numbers greater than approximately two are sufficient for the formation of vortices. Since the flow over a cylinder and the oscillations of coalescing droplets each involves direction-changing flow, the formation of vortices, may be occurring during the droplet-fusing process, and the convective motions of such vortices would enhance the mixing process.

Figure 4:
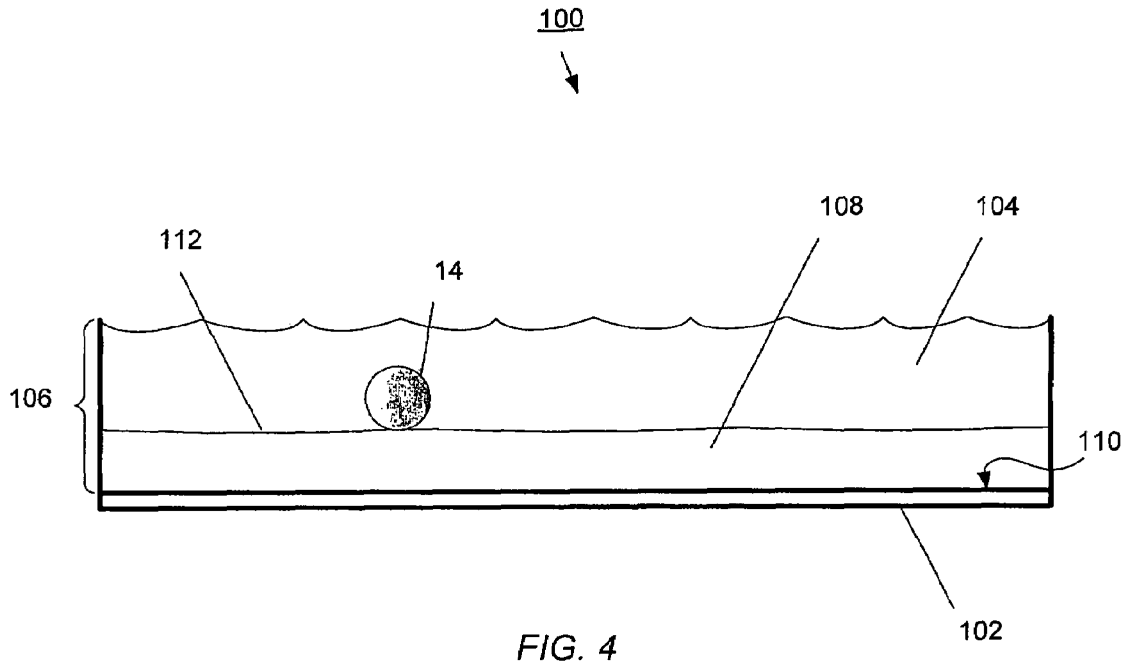
FIG. 4 is a diagram illustrating an embodiment of three-fluid system for use in moving droplets using a laser beam in accordance with the invention.

FIG. 4 shows an embodiment of a system 100 that can be used to avoid contact between the droplet 14 and the surface 8 of the substrate 10 (which may be desirable in order to avoid bio-fouling of the droplet contents with the surface). In this embodiment, a standard polystyrene Petri dish 102 holds a liquid phase 106 comprised of a first immiscible liquid 104 and a second immiscible liquid 108. The second immiscible liquid 108 has a greater density than the first immiscible liquid 104 and produce a fluid-to-fluid interface 112 upon which the droplet 14 rests when deposited in the liquid phase. In effect, the droplet 14 is suspended above the bottom surface 114 of the Petri dish 102 within the liquid phase 106. In one embodiment, the first immiscible liquid 104 is 1-decanol and the second immiscible liquid 108 is perflourinated silicone oil. This system 100 does not exhibit a contact angle hysteresis, thus reducing the force needed to move droplets along the fluid-to-fluid interface 112. Dedicated optical traps or electrostatic trapping techniques can be used (in conjunction with the droplet movement techniques of the present invention) to overcome any convection currents or thermal Brownian motion that may affect precise droplet control.

Figure 5:
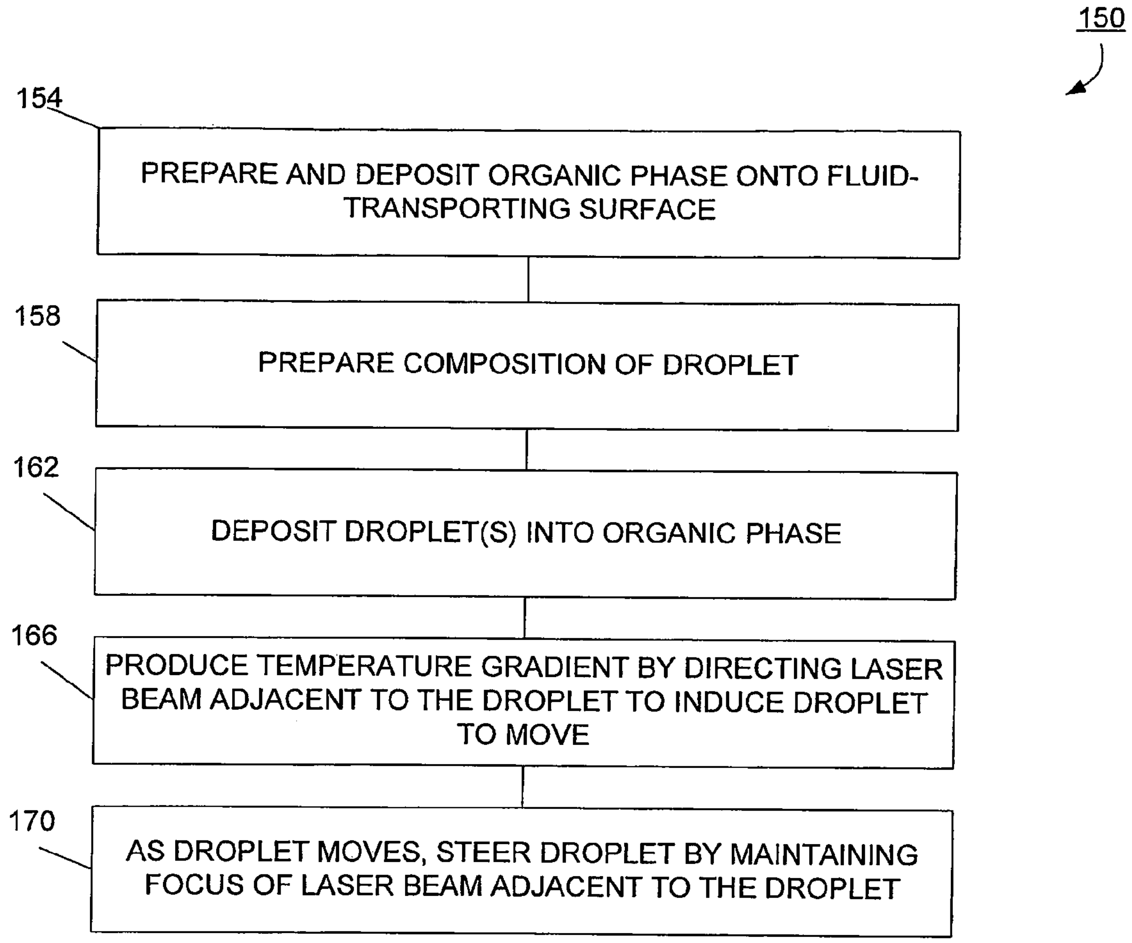
FIG. 5 is a flow diagram of an embodiment of a process for optically moving droplets in accordance with the invention.

FIG. 5 shows a process 150 for optically performing microfluidic operations, such as moving, fusing, and mixing micro-droplets, in accordance with the principles of the invention. The particular numbering of the steps of the process 150 does not necessarily imply any particular order in the performance of these steps. At step 154, provided on a surface is a liquid phase comprised of one or more immiscible liquids.

At step 158, prepared and readied for use are the fluids to be manipulated, e.g., samples and reagents, in accordance with the invention. For example, preparation can entail determining the particular composition of the various samples and various reagents and depositing these fluids in respective sample and reagent wells on a microfluidic device or lab-on-a-chip. At step 162, deposited into the liquid phase are one or more droplets. Such droplets can be samples and reagents drawn from respective wells of a microfluidic device. Examples of techniques for depositing a droplet onto the surface include using a 34-gauge needle (100-micron inner diameter) and directly injecting the droplet from a standard inkjet print head. Other techniques can include the use of printing pins, pipettes, and/or syringes.

At step 166, focused adjacent to an edge of one of the droplets on the surface is a laser beam. The laser beam may pass through the droplet, causing the droplet to heat (e.g., through optical absorption of molecules within the droplet or vibration of the water O—H stretch). This heating causes a thermal gradient to form across the droplet, which produces a surface tension across the droplet surface that induces the droplet to move. Alternatively, the laser beam does not pass through the droplet, but passes near the droplet such that the thermal gradient produced in the surrounding liquid phase is sufficient to induce the droplet to move. As the droplet moves, maintaining focus of the laser beam adjacent to the rear (i.e., receding) edge of the droplet steers(step 170) the droplet in a desired direction. For example, the droplet can be moved into a given mixing well of the microfluidic device (to fuse with a droplet already in the well or with a droplet to be moved subsequently into the well). Each well needs not be an actual physical well. The restraining force of contact angle hysteresis may define the location of a well, once the laser is no longer moving the droplet. Microfluidics devices of the invention have a plurality of such mixing wells (e.g., arranged in a two-dimensional array) to enable personnel to perform parallel assays. Researchers can thus draw droplets of sample and reagent fluids from any one of the respective wells, deposit these droplets onto the microfluidics device surface, and move the droplets, as described above, into any given mixing well in accordance with any preferred configuration. Processing of droplets may be performed in an automated fashion, for example with computer control, to avoid direct human interaction when processing very large numbers of droplets.

Heating droplets may be used to perform other functions. For example, in a polymerase chain reaction (PCR) process, thermal cycling is used to perform amplification of DNA, and laser heating may be used to perform the heating for PCR. Heating without moving the droplet may be achieved by using a laser beam with a hole at the center (a "doughnut" beam). Positioning the laser beam so that the position of the droplet is at the hole in the laser beam results in a situation where the droplet cannot move. Turning the laser beam on and off, repetitiously, results in thermal cycling. The power of the laser and the period for which the laser beam is on control the temperature reached in the droplet. The doughnut beam shape may also be achieved by moving the steering means (42 in FIG. 1) in a circular fashion at a faster rate than the droplet can move.

While the invention has been shown and described with reference to specific preferred embodiments, it should be understood by those skilled in the art that various changes in form and detail may be made therein without departing from the spirit and scope of the invention as defined by the following claims.

What is claimed is:

1. A method of moving droplets, comprising:

providing a liquid phase on a surface;

dispensing a droplet into the liquid phase, the liquid phase being immiscible with the droplet; and directing a focused beam of light into direct contact with an edge region of the droplet in the liquid phase causing the droplet to heat and a thermal gradient to form within the droplet sufficient to induce the droplet to move in the liquid phase.

2. The method of claim 1, wherein the droplet forms a contact angle approaching 180° with respect to the surface.

3. The method of claim 1, wherein the surface of a substrate upon which the liquid phase is disposed, the substrate being transparent to a wavelength of the light beam so that the light beam passes through the substrate to come in direct contact with the droplet.

4. The method of claim 1, wherein the immiscible liquid phase includes an organic liquid.

5. The method of claim 4, wherein the organic liquid includes decanol.

6. The method of claim 1, wherein the immiscible liquid phase controls evaporation of the droplet.

7. The method of claim 1, wherein the immiscible liquid phase comprises a first immiscible liquid and a second immiscible liquid, the second immiscible liquid having a greater density than that of the first immiscible liquid and of the droplet to produce a fluid-to-fluid interface between the immiscible liquids upon which the droplet sits.

8. The method of claim 7, wherein the second immiscible liquid includes perflourinated silicone oil.

9. The method of claim 1, wherein the droplet is aqueous.

10. The method of claim 1, wherein the beam of light includes an infrared wavelength.

11. The method of claim 1, further comprising inserting dye into one of the droplet and the immiscible liquid phase to cause optical absorption by molecules of the dye.

12. The method of claim 1, wherein a size of the droplet ranges from approximately 30 μm to 1500 μm in diameter.

13. The method of claim 1, wherein the droplet is a first droplet, and further comprising depositing a second droplet into the immiscible liquid phase and moving the first droplet into the second droplet to cause the droplets to fuse and contents of the droplets to mix.

14. The method of claim 13, wherein each droplet contains a chemical fragment.

15. The method of claim 13, further comprising detecting a biological molecule in the fused droplet.

16. The method of claim 13, further comprising detecting a gene in the fused droplet.

17. The method of claim 13, further comprising detecting products of gene expression of a particular gene.

18. The method of claim 1, further comprising turning the light beam on and off to perform thermal cycling of the droplet.

19. An apparatus for moving droplets, comprising:

a liquid phase on a surface;

a droplet disposed in the liquid phase;

a light source producing a focused beam of light;

means for directing the focused beam of light into direct contact with an edge region of the droplet disposed in the liquid phase causing the droplet to heat and a thermal gradient to form within the droplet sufficient to induce the droplet to move within the liquid phase.

20. The apparatus of claim 19, wherein the liquid phase is immiscible with the droplet, and wherein the droplet is surrounded by the immiscible liquid phase.

21. The apparatus of claim 19, wherein the liquid phase comprises a first immiscible liquid and a second immiscible liquid, the second immiscible liquid having a greater density than that of the first immiscible liquid and of the droplet to produce a fluid-to-fluid interface between the immiscible liquids upon which the droplet sits.

22. The apparatus of claim 21, wherein the second immiscible liquid includes perflourinated silicone oil.

23. The apparatus of claim 20, wherein the immiscible liquid phase includes an organic liquid.

24. The apparatus of claim 23, wherein the organic liquid includes decanol.

25. The apparatus of claim 19, where the beam of light includes an infrared wavelength.

26. The apparatus of claim 19, wherein the droplet is aqueous.

27. The apparatus of claim 19, wherein the droplet includes a dye to cause optical absorption by the droplet.

28. The apparatus of claim 19, wherein a size of the droplet ranges from approximately 30 μm to 1500 μm in diameter.

29. The apparatus of claim 19, further comprising a second droplet disposed in the liquid phase and wherein the directing means causes one of the droplets to move into the other of the droplets, causing the droplets to fuse and contents of the droplets to mix.

30. The apparatus of claim 29, wherein each droplet contains a chemical fragment.

31. The apparatus of claim 29, further comprising means for detecting a biological molecule in the fused droplet.

32. The apparatus of claim 29, further comprising means for detecting a gene in the fused droplet.

33. The apparatus of claim 29, further comprising means for detecting products of gene expression of a particular gene.

34. The method of claim 19, wherein the surface is a surface of a substrate upon which the liquid phase is disposed, the substrate being transparent to a wavelength of the light beam so that the light beam passes through the substrate to come in direct contact with the droplet.

* * * * *

UNITED STATES PATENT AND TRADEMARK OFFICE
CERTIFICATE OF CORRECTION

PATENT NO. : 7,582,858 B2
APPLICATION NO. : 10/597372
DATED : September 1, 2009
INVENTOR(S) : Gregory Faris, Kenneth T. Kotz and Kyle Noble It is certified that error appears in the above-identified patent and that said Letters Patent is hereby corrected as shown below:

In column 4, line 39, "aperature" should be changed to --aperture--.

In column 6, line 5, "HP" should be changed to --HRP--.

In column 6, line 37, delete the "," after "vortices".

In column 8, claim 3, line 13, after "surface" insert --is a surface--.

In column 10, claim 34, line 14, "method" should be changed to --apparatus--.

Signed and Sealed this

Twenty-sixth Day of January, 2010

David J. Kappos

David J. Kappos
*Director of the United States Patent and Trademark Office*